United States Patent [19]
McKenzie et al.

[11] Patent Number: 5,798,097
[45] Date of Patent: Aug. 25, 1998

[54] IMMUNOGOBULIN CONJUGATES

[75] Inventors: Ian Farquhar Campbell McKenzie; Geoffrey Allan Pietersz; Mark John Smyth, all of Parkville, Australia

[73] Assignee: Pharmacia & Upjohn S.p.A., Milan, Italy

[21] Appl. No.: 420,712

[22] Filed: Apr. 11, 1995

Related U.S. Application Data

[63] Continuation of Ser. No. 927,541, Jul. 24, 1992, abandoned, which is a continuation of Ser. No. 796,884, Nov. 25, 1991, abandoned, which is a continuation of Ser. No. 167,122, Mar. 11, 1988, abandoned.

[30] Foreign Application Priority Data

Mar. 11, 1987 [AU] Australia ................. PI0803
Jul. 7, 1987 [AU] Australia ................. PI2955

[51] Int. Cl.$^6$ .............. A61K 39/395; A61K 39/44; C07K 16/00; C07K 17/00
[52] U.S. Cl. .................. 424/181.1; 424/178.1; 424/179.1; 530/391.7; 530/391.9
[58] Field of Search .............. 530/391.1, 391.7, 530/391.9; 424/178.1, 179.1, 181.1

[56] References Cited

U.S. PATENT DOCUMENTS

| | | | |
|---|---|---|---|
| 4,077,988 | 3/1978 | Arcamone et al. | 552/201 |
| 4,867,973 | 9/1989 | Goers et al. | 424/85.91 |
| 4,950,738 | 8/1990 | King et al. | 530/322 |

FOREIGN PATENT DOCUMENTS

| | | | |
|---|---|---|---|
| 122132 | 6/1984 | European Pat. Off. | |
| 208615 | 3/1986 | European Pat. Off. | |
| 0208615 | 1/1987 | European Pat. Off. | A61K 47/00 |
| 0294294 | 12/1988 | European Pat. Off. | |
| 0155334 | 7/1986 | Japan | |
| 1541436 | 2/1975 | United Kingdom | |
| 2158078 | 11/1985 | United Kingdom | |

OTHER PUBLICATIONS

Osband et al (1990) Immunology Today 11(6):193–195.
Gould et al (1989) J. Natl. Cancer Inst. 81(10):775–781.
Harris et al (1993) TIBTECH 11:42–44.
Hermentin et al (1988) Behring Inst. Mitt. No. 82:197–215.
Waldmann (1991) Science 252:1657–1662.
Sally Seaver (1994) Aug. issue of Genetic Engineering News pp. 10 and 21.
Pastan et al 47:641–648 of Cell 1986.
E. Diener et al. (1986) Science 231: 148–150.
J. Gallego et al. (1984) Int. J. Cancer 33: 737–744.
S. Xie et al. (1987) Transplantation 44:770–774.
Pietersz; Smyth; McKenzie—Cancer Res (U.S.A) 1988 48/4 pp. 926–931 Coden CNREA.
Pietersz; Smyth: McKenzie. J. Natl. Cancer. Inst. (U.S.A.) 1987 pp. 1367–1373. Coden JNCIA.
Gerbino: Am Drug (U.S.A.) 1984 190/2 pp. 58–64 Coden AMDRA.
Antibody, Immunconjugates and Radiopharmaceuticals, vol. 1, No. 1, 1988, pp. 79–102, Mary Ann Liebert Inc. Publishers; g.A. Pietersz et al.: Preclinical and clinical studies with a variety of immunoconjugates . . . .
Transplantation, vol. 46, No. 1, juillet 1988 pp. 126–131. US; M.J. Smyth et al.: Immunosuppression of graft rejection with . . . .
Br. J. Cancer, vol. 47, 1983, C.H. Thompson et al: "Monoclonal antibodies to human colon and colorectal carcinoma".

*Primary Examiner*—Ponnathapura Achutamurthy
*Attorney, Agent, or Firm*—Oblon, Spivak, McClelland, Maier & Neustadt, P.C.

[57] ABSTRACT

Immunoglobulin conjugates, comprising idarubicin (Ida) conjugated to a monoclonal antibody or fragment thereof comprising at least one of the antigen binding sites of the antigen, are useful for treating a human or other animal suffering from a cancer or for depleting a subset of T lymphocytes from a population of cells.

12 Claims, 10 Drawing Sheets

A  IDARUBICIN       R = H
B  BROMOIDARUBICIN  R = Br
C  AMINE LINK       R = NH—MoAb
D  ESTER LINK       R = O—C(=O)—MoAb

Fig. 1.

| A | IDARUBICIN | R = H |
| B | BROMOIDARUBICIN | R = Br |
| C | AMINE LINK | R = NH—MoAb |
| D | ESTER LINK | R = O—C(=O)—MoAb |

IMMUNOGOBULIN CONJUGATES

This application is a continuation of application Ser. No. 07/927,541, filed on Jul. 24, 1992, now abandoned, which is a continuation of application Ser. No. 07/796,884, filed on Nov. 25, 1991, now abandoned, which is a continuation of application Ser. No. 07/167,122, filed on Mar. 11, 1988, now abandoned.

This invention relates to immunoglobulin conjugates, their preparation and their use.

The general concept of targeting antineoplastic agents to tumours using monoclonal antibodies (MoAbs) is known and its therapeutic significance is currently being evaluated. Generally the approach involves producing conjugates of antibody and a toxic agent, capable of selectively localizing and damaging tumour cells. Major attention has been directed towards constructing immunotoxins from A chains of plant and bacterial toxins and antibodies, such that their antigen binding and internalization leads to cell death. In practice, many MoAbs believed to be specific for tumours are also reactive with subpopulations of normal cells and consequently it may be unrealistic to utilize such potent toxins because of their potential damage to normal tissues. A safer alernative to plant toxins has been to couple antibodies to conventional anti-cancer drugs such as doxorubicin, vindesine, chlorambucil, melphalan and methotrexate. Due to the non-specific toxic effects of the currently used antineoplastic agents, there have been attempts to increase their therapeutic index by coupling them to MoAbs to tumour antigens.

Attempts to suppress thymus-derived T cell graft rejection have often focused on reducing T cell activity by using antithymocyte globulin. More recently, with the development of monoclonal antibodies, it has been possible to define T cell subsets according to their function in vitro and to the presence of specific surface antigens defined by MoAb. This has stimulated the search for a mechanism by which T cells control graft rejection, concentrating on the major division into the helper/inducer and cytotoxic/suppressor subsets defined by the L3T4 and Ly-2 murine antigens. Although the OKT3 MoAb, an anti-pan T cell reagent, has proven in vivo potency, in a recent study we found that 20 MoAbs to 20 different murine lymphocyte antigens were without in vivo effect in mice and are therefore useless for in vivo studies. It is therefore appropriate to examine means by which these highly specific MoAbs can be rendered more potent and completely remove their target cells. The use of cytotoxic drugs coupled to MoAbs is one such approach.

The clinical potential of drug-MoAb conjugates includes the immunochemotherapy of cancer and the alleviation of various immunoregulatory disorders and allograft rejection. Many studies have demonstrated the specific cytotoxicity of toxins and drugs on tumour cells when coupled to MoAb raised to tumour-associated antigens. However, less emphasis has been directed towards the in vivo use of drug-MoAb conjugates to eradicate T cells and to investigate T cell immunoregulation in graft rejection, although toxin-antibody conjugates have been used extensively in vitro to eradicate T cells prior to bone marrow transplantation.

Anthracyclines are an important group of antineoplastic agents used in the chemotherapy of cancer, of which doxorubicin and daunorubicin have shown efficacy towards solid tumours. Coupling of daunorubicin and doxorubicin to antibodies, however, results in a substantial loss of drug activity when coupling is carried out via the amino group. Recently, daunorubicin has been coupled to MoAbs via carbon atom 14 using bromodaunorubicin. These conjugates demonstrated activity in vitro. However, no in vivo studies were reported (Gallego et al, Int. J. Cancer, 1984 33 737–744). Further, it has been shown that daunorubicin-MoAb conjugates demonstrate a non-specific toxicity at concentrations >10 µg/ml.

We have now found that Idarubicin (4-demethoxy-daunorubicin, Ida) may be coupled to MoAbs and that the conjugates have a selective and potent in vitro and in vivo anti-tumour activity. Non-specific toxicity of Ida-MoAb conjugates has not been evident in vivo at doses of <8.0 mg/kg. The Ida-MoAb conjugates possess greater in vitro and in vivo efficacy than daunorubicin-MoAb conjugates.

Further, we assessed the ability of Ida-MoAb conjugates specifically to eradicate cell populations by coupling Ida to MoAbs known to react with different subpopulations of lymphocytes (L3T4$^+$, Ly-2$^+$ and Thy-1$^+$). We have found this to be a surprisingly effective method of depleting cells. For example the anti-Ly-2.1 MoAb, which has no measurable effect in vivo on Ly-2.1$^+$ cells, can be converted to an effective cytotoxic agent by coupling with the cytotoxic agent Ida.

Using MoAbs to Ly-2 and L3T4 antigens, we have now demonstrated that Ida-MoAb can eliminate target cells in vitro and in vivo. Ida-MoAb conjugates can be provided which have greater potential to deplete specifically T cell subsets responsible for graft rejection than antilymphocyte globulins or anti-pan-T-cell reagents such as OKT3 MoAb.

Accordingly the present invention provides immunoglobulin conjugates comprising Ida conjugated to a monoclonal antibody or fragment thereof comprising at least one of the antigen binding sites of the antibody.

Ida is described in U.S. Pat. No. 4077988. Preferably from two to eight Ida molecules are covalently linked to each antibody or antibody fragment molecule, more preferably from two to six. The Ida molecules are generally, but-not necessarily, conjugated at the 14-position to the monoclonal antibody or antibody fragment. Preferably they are directly linked, although it is possible to interpose an inert carrier or linker. The Ida may however be bound to the monoclonal antibody or antibody fragment via the amino group instead. This may be achieved using a degradable peptide spacer, a dextran carrier, an acid-sensitive spacer or poly-glutamic acid. Groups used for linking include the carboxylic acid groups of synthetic polyamino acids such as poly-L-glutamic acid and poly-L-aspartic acid or inert proteins such as human serum albumin or functionalized dextrans such as carboxymethyl dextran can act as carriers. These carriers may range in size from 10–60 kilodaltons.

Typically each antibody or antibody fragment is specific for an antigen on the surface of cells against which it is wished to target Ida. For example, the antibody or antibody fragment may be specific for a desired target tissue such as a human neoplasm. Examples of human neoplasms against which it may be wished to target Ida are breast, colon, lung, prostatic, ovarian, thymus and other cancers, sarcomas and leukaemias. The antibody or antibody fragment may alternatively be specific for an animal neoplasm. An antibody or antibody fragment specific for human transferrin receptor (TFR), which is present on dividing cells, erythroid precursor cells and cells of a variety of tumours, may be used. A suitable anti-TFR monoclonal antibody may one raised against the transferrin receptor on LiCR-LON-HMy-2 (HMy-2) cells.

When the immunoglobulin conjugates are intended for use in depleting a specific T lymphocyte population, the antibody or antibody fragment is specific for a cell surface antigen which is itself specific for those T lymphocytes. The antibody or antibody fragment may therefore be specific for a population of helper, suppressor or cytotoxic T lymphocytes.

Preferably, the monoclonal antibody or antibody fragment is of the same species as that to which the immunoglobulin conjugate is to be administered. A human or mouse monoclonal antibody or antibody fragment is therefore typically employed where it is intended to administer the conjugate to humans. Also preferably, the antibody or antibody fragment is of the IgG class. The antibody fragment may be the Fab, Fab' or F(ab')$_2$ fragment. IgM monomer, which can be derived from IgM antibody by proteolytic enzyme digestion, may also be employed.

The immunoglobulin conjugates are prepared according to the invention by a process comprising conjugating Ida to the monoclonal antibody or fragment thereof. Preferably, a 14-halo-Ida is reacted with the monoclonal antibody or fragment thereof. The 14-substituent may be fluorine, chlorine, bromine or iodine but is preferably bromine. 14-Bromo-Ida is described in U.S. Pat. No. 4125607. Conjugation may therefore be achieved by a process comprising:

(a) mixing the monoclonal antibody or fragment thereof with a molar excess of 14-halo-Ida,
(b) reacting the mixture at from 18° to 37° C.,
(c) removing any precipitate,
(d) removing unreacted starting materials by gel filtration, and
(e) removing adsorbed drug (Ida) by adsorption chromatography or ion exchange chromatography.

Step (a) is typically effected in a water-miscible organic solvent such as N,N-dimethylformamide. Preferably the molar excess of the 14-halo-Ida in step (a) is from 0 to 50 fold. In step (b), preferably the reaction is effected for a period of from 1 to 8 hours. Typically the reaction temperature is room temperature.

Other methods of conjugation may be used, however. Where a conjugate is required having an inert carrier or linker interposed between the Ida and the monoclonal antibody or antibody fragment, the carrier or linker typically is first attached at the C-14 carbon atom of Ida and then linked to the antibody or antibody fragment. Also, as mentioned above the antibody or antibody fragment may be bound to Ida via the amino group using a degradable peptide spacer, a dextran carrier, an acid-sensitive spacer or poly-glutamic acid.

The immunoglobulin conjugates of the invention can be used to treat a human or other mammal suffering from a cancer. A therapeutically effective amount of the conjugate can be administered. The cancer may be a solid tumour, an ascites tumour or a leukaemia. Human neoplasms which may be treated are mentioned above. Two or more conjugates may be administered in which the monoclonal antibody or antibody fragment in each conjugate has a different specificity.

A conjugate may be administered by injection. It can be given parenterally, for example intravenously. It may be administered locally or directly into the tumour. The amount of a conjugate administered to a patient will depend upon a variety of factors such as the tumour being treated and the condition of the patient. Typically, however, a dose from 10 to 200 mg of conjugate may be administered per m$^2$ of a patient's body area. The conjugates may be administered with other chemotherapeutic agents or with agents which enhance the activity of the conjugates, e.g., vasoactive agents or Tumour Necrosis Factor.

The immunoglobulin conjugates can also be used for specifically depleting a subset of T lymphocytes from a population of cells. A therapeutically effective amount of a conjugate, incorporating a monoclonal antibody or antibody fragment directed against a cell surface antigen present on the lymphocytes to be depleted, may be administered to a human or animal. Alternatively, a cell population may be incubated in vitro with such a conjugate.

A combination of conjugates directed against two or more cell surface antigens may be used. The lymphocytes to be depleted may be helper, suppressor or cytotoxic T cells.

This aspect of the invention may be used to prevent rejection of grafted tissue in a graft recipient. The conjugates may be used as immunosuppressive agents. An amount of conjugate effective to prevent graft rejection is administered to the graft recipient. Preferably it is cytotoxic T cells which are depleted in this instance. A human or animal with a cancer may be treated by depleting suppressor T cells by administration of an appropriate conjugate. Autoimmune diseases can be treated by administering a conjugate for the purpose of depleting helper T cells. In each instance, the route of administration and dose of conjugate are as mentioned above.

The immunoglobulin conjugates are formulated as pharmaceutical compositions with a pharmaceutically acceptable carrier or diluent. Any appropriate carrier or diluent may be used. Suitable carriers and diluents include physiological saline solution and Ringers dextrose solution.

BRIEF DESCRIPTION OF THE DRAWINGS

The following Examples illustrate the invention. In the accompanying drawings, FIGS. 1 to 12 relate to Example 1 and FIGS. 13 to 17 relate to Example 2. More particularly.

EXAMPLE 1

Materials and Methods

Tumour Cells

The cell lines examined in this study included the (Ly-2$^+$) murine thymoma ITT(1) 75NS E3 variant (E3) (Smyth et al, J. Natl Cancer Inst. 1986 76 503–510), the (Ly-2$^-$, TFR$^-$) lymphoma EL4 (Horowitz et al, Science 1968 160 533–535), the (TFR$^+$) human cell line CEM (Foley et al Cancer 1965 18 522–529) and the (250-30.6$^+$) human cell line COLO 205. Cells were maintained in vitro in Dulbecco's Modified Eagle's medium (DME) or RPMI 1640 medium (Flow Laboratories, Sydney, Australia), supplemented with 10% heat inactivated newborn calf serum (Flow), 2 mM glutamine (Commonwealth Serum Laboratories, Sydney, Australia); 100 ug/ml streptomycin (Glaxo, Melbourne, Australia) and 100 I.U./ml penicillin (Commonwealth Serum Laboratories). The E3 tumour was maintained in vivo by serial passage into (C57BL/6×BALB/c)F$_1$ mice (CBF$_1$ mice). Cells from the ascites fluid were washed and centrifuged (400 g×5 min) twice in phosphate buffered saline (PBS), pH7.3, resuspended in PBS and injected subcutaneously (s.c.) into the abdominal wall of mice; these developed into palpable tumours prior to treatment. Mice were subjected to a series of intraveneous (i.v.) or intratumour (i.t.) treatments and the subsequent size of tumours was measured daily with a caliper square, measuring along the perpendicular axes of the tumours. Data was recorded as mean tumour size (product of two diameters ± standard error).

Mice

CBA and (C57BL/6xBALB/c) mice (CBF$_1$ mice) and nude (nu/nu) mice were produced in the Department of Pathology, University of Melbourne. Experimental groups of 8–10 mice all of the same sex and age were used in each experiment.

Monoclonal Antibodies

MoAbs used were: (i) Anti-Ly-2.1 (IgG1) reactive with the murine Ly-2.1 specificity (Hogarth et al Immunology 1982 46 135–144) and (ii) A3C6 (anti-TFR) (IgG1) reactive with the human transferrin receptor (TFR) (Panaccio et al Immunology and Cell Biology 65, 461–472, 1987); and (iii) an antibody, designated 250-30.6, reactive against an antigen present on human colon carcinoma cells.

The MoAbs were isolated from ascites fluid by precipitation with 40% ammonium sulphate, dissolution in PBS and dialysis with the same buffer. These crude preparations were either absorbed on to Protein-A-Sepharose (Pharmacia Inc., Piscataway, N.J.), washed extensively with PBS (pH 7.3) and eluted with 0.2M glycine/HCl (pH 2.8), or passed through an Affigel blue column (Bio-Rad Laboratories Pty. Ltd., Sydney). Following neutralization, MoAbs were then dialysed against PBS, aliquoted and stored at −70° C. A3C6 was obtained by immunising CBA mice intraperitoneally at weekly intervals for three weeks with $2 \times 10^6$ LiCR-LON-HMy-2(HMy-2) cells (OKT9$^{+*}$), removing the spleens three days after the last injection and fusing with P3-NSI-AG4-1 (NS-1) cells.

Preparation and Quantitation of Conjugates

Intact anti-Ly-2.1, anti-TFR MoAb, or 250-30.6 (1–2 mg/ml in borate buffer pH 8.0) was mixed with a molar excess (1–50) of 14-bromo-4-demethoxydaunorubicin (Br-Ida) dissolved in (N,N)-dimethylformamide (DMF) at 10 mg/ml. The reaction was maintained at room temperature for 4 hours before centrifuging (400 g×5 minutes) to remove any precipitate. Free Br-Ida and other unreacted starting materials were removed by gel filtration chromatography using a Sephadex G-25 column (PD-10; Pharmacia) and the conjugates were then passed through a column of Porapak Q (Millipore) to remove any adsorbed drug (Niederwieser et al. J. Chromatog. 1971 54 215–223). The amount of Ida incorporated in drug-MoAb conjugates was determined by absorbance spectrophotometry at 483 mm ($E_{498}=3.4 \times 10^3 M^{-1} cm^{-1}$) and by protein estimation (Bradford, Anal. Biochem. 1976 72 248–253).

Antibody Activity

A rosetting assay using sheep anti-mouse immunoglobulin (SAMG) was used to determine the antibody activity of Ida-MoAb conjugates compared with free MoAb which had undergone the same procedures used in the coupling method (Parish and McKenzie, J. Immunol. Methods 1978 20 173–183).

Drug Activity (a) 24 hour inhibition assay: 100 ul of cells ($2-5 \times 10^6$/ml) were added to a flat-bottomed microtitre plate and incubated for 1 hour at 37° C. Free Idarubicin (Ida) (dissolved in PBS) and Ida-MoAb conjugates were filtered aseptically and dilutions were performed in sterile PBS; 50 ul of free Ida or conjugate were added to the cells using duplicate wells for each sample; control wells received 50 ul of PBS and the cells were cultured at 37° C., 7% $CO_2$ for 24 hours.

(b) 30 minute inhibition assay: 200 ul of cells ($2-5 \times 10^6$/ml) were collected in sterile Eppendorf tubes, resuspended in sterile drug or conjugate and mixed for 30 min at 37° C. Cells were then centrifuged (400 g×5 min), resuspended in growth medium and 100 ul aliquots were seeded into a microtitre plate using duplicate wells for each sample before an incubation period of 16–24 hours. After the incubation period in both these assays, 50 ul of growth medium containing 1 uCi of [$^3$H]-thymidine (specific activity=5 Ci/mmol; Amersham) was added and the plates incubated for 2–4 hours. Cells were then harvested and dried, and individual samples were separated and counted on a beta scintillation counter. Incorporation of [$^3$H]-thymidine was expressed as a percentage inhibition in incorporation of controls. Standard error for any point was generated by duplicate determinations and did not exceed 5% for any given experimental point.

Toxicity

Groups of 10–20 CBA mice were given a single i.v. injection of various doses of Ida or Ida-anti-Ly-2.1 and the survival of mice was recorded against the dose of drug delivered in mg/kg. The organs of these mice were removed and weighed prior to formalin fixation and staining by haematoxylin and eosin.

RESULTS

Preparation and Characterization of Conjugates

Figure 1:
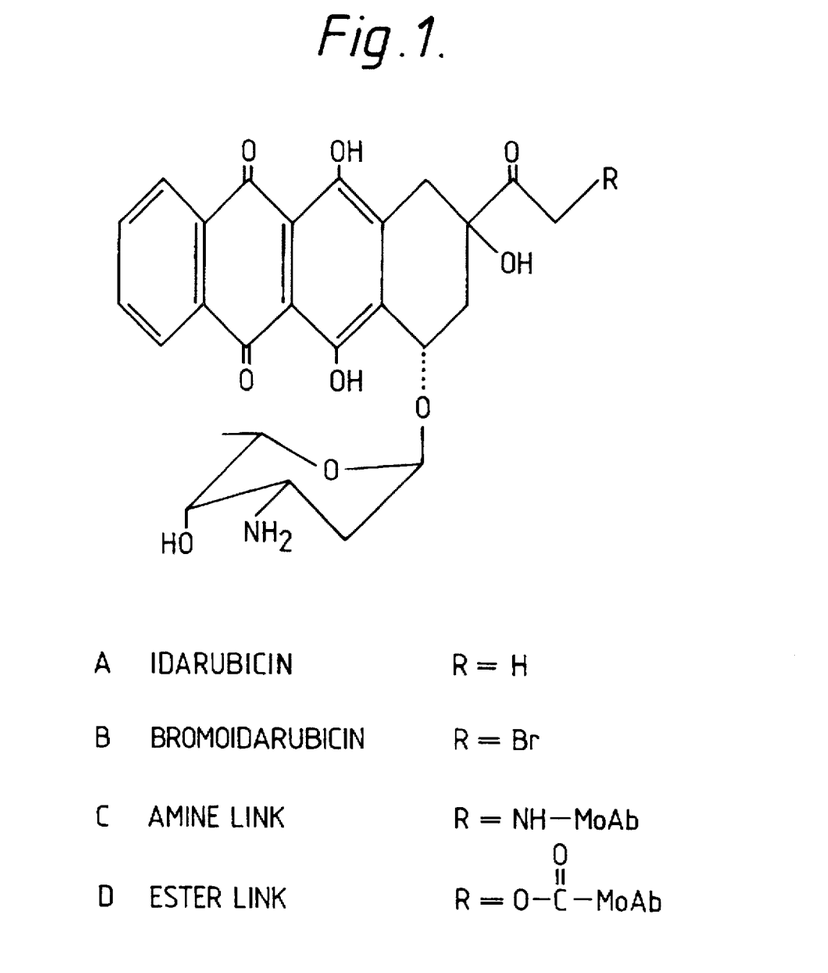
FIG. 1 represents the structure of anthracycline derivatives.
Figure 2:
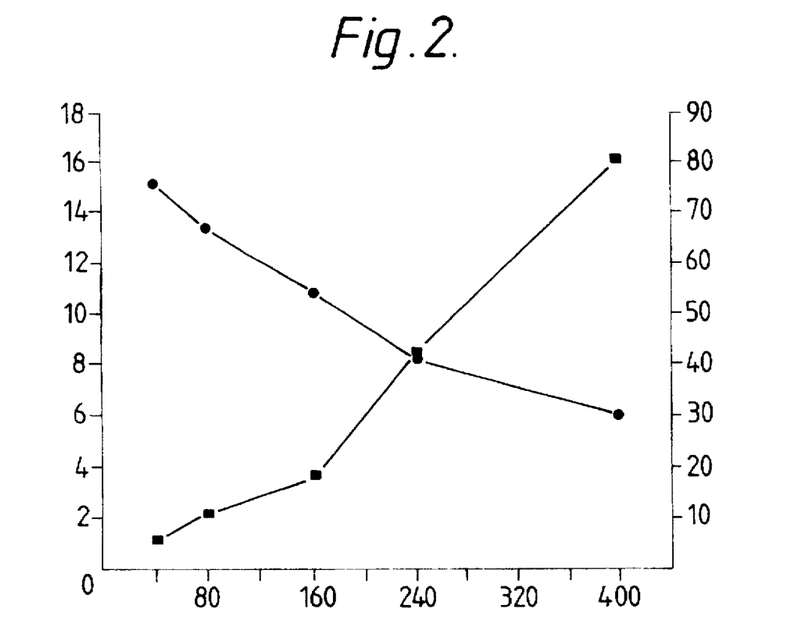
FIG. 2 represents the coupling of Idarubicin (Ida) to anti-Ly-2.1 (0.5 mg). Moles of Ida incorporated per mole of anti-Ly-2.1 (■) (left hand ordinate) and protein recovery (●) (right hand ordinate) are shown as a function of the number of nmoles of Ida in the reaction mixture (abscissa)

Br-Ida (FIG. 1) was covalently coupled to several MoAbs: against the human TFR, against an antigen present on human colon cancer cells (antibody 250-30.6), and against the murine Ly-2 alloantigen. Reaction conditions were established for the conjugation by varying the molar excess of Br-Ida added to MoAbs and making a compromise between higher Ida incorporation and lower protein recoveries. Ida-anti-Ly-2.1 (FIG. 2), Ida-anti-TFR and Ida-250-30.6 (data not shown) incorporated 3 to 5 molecules of Ida with protein recoveries of greater than 50%. Reaction of Br-Ida with MoAbs could give rise to two types of linkages (FIG. 1C and D). To establish which was present, conjugates were exposed to pH 4.5 or pH 9.0 for 48 hours, free drug released was absorbed into Porapak Q and the samples were requantitated by spectrophotometry. Fifty percent of the bound drug was released on exposure to base (pH 9.0), while no loss was apparent at pH 4.5. This would suggest that at least 50% of the drug is ester linked (FIG. 1D) as the ester linkage is sensitive to basic conditions whilst the amine link is stable.

Antibody Activity

Figure 3:
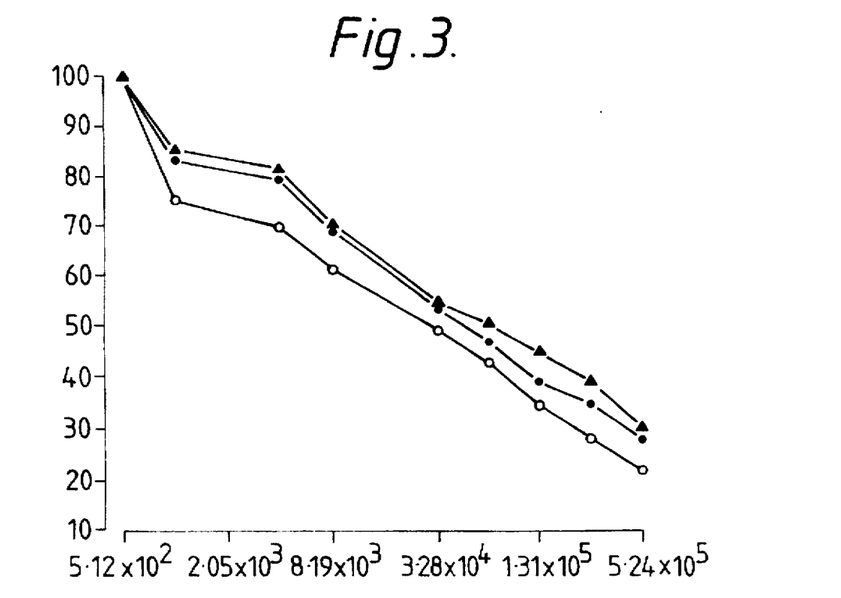
FIG. 3 represents the antibody titre measured as the % rosette forming cells (ordinate) versus antibody dilution (−1)(abscissa) of anti-Ly-2.1 conjugates on ITT(1) 75 NS E3 target cells. Serial dilutions were performed upon a 0.5 mg/ml solution of either anti-Ly-2.1 (▲) or anti-Ly-2.1 with 2 (●) or 8 (○) mol Ida/mol antibody.

The titres of antibody before and after conjugation were measured by the resetting method and were determined as the dilution at which 50% of the target cells demonstrated rosettes. Ida-anti-Ly-2.1 conjugates containing 2 and 8 molecules of Ida had antibody titres against E3 cells of 1:56,000 and 1:33,000 respectively, whilst the non-conjugated antibody titre was 1:80,000 (FIG. 3). Ida-250-30.6 conjugates containing 2 and 6 molecules of Ida had antibody titres against COLO 205 cells of 1:16,000 and 1:11,000 respectively, whilst the non-conjugated antibody titre was 1:33,000. Thus there is some loss of antibody activity due to the conjugation procedure; conjugates with less than 6 molecules of Ida-molecule of MoAb were used for in vitro and in vivo studies. It was noted that the solubility and antibody activity of Ida-anti-Ly-2.1 conjugates decreased significantly beyond these levels of Ida incorporation (data not shown). The maximum number of Ida molecules which may usefully be incorporated will vary, depending on the individual antibody.

In Vitro Activity and Idarubicin and Idarubicin-MoAb Conjugates

Figure 4:
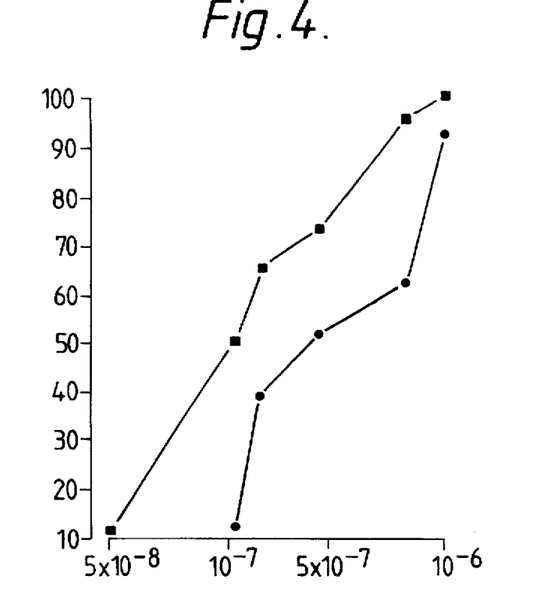
FIG. 4 represents the inhibitory effect of Ida (■) or Ida-anti-Ly-2.1, 5 mol Ida/mol antibody, (●) on E3 cells in a 24 hour assay where % inhibition in [$^3$H] thymidine incorporation (ordinate) is plotted against concentration of Ida(M)(abscissa)

The in vitro cytotoxicity of Ida and two Ida-MoAb conjugates on the murine ITT(1)75NS E3 cell line (Ly-2$^+$ TFR$^-$) and the human CEM cell line (Ly-2$^-$TFR$^+$) was measured in a 24 hour inhibition assay and values for LD$_{50}$ (50% inhibition in [$^3$H]-thymidine incorporation of controls) were determined. Results are shown in FIG. 4 and Table 1. The LD$_{50}$ for Ida was in the range of 1.0 to $2.5 \times 10^{-7}$M for both cell lines tested (FIG. 4, Table 1). The I.D$_{50}$ for Ida-anti-Ly-2.1 on E3 was 4 times greater (FIG. 4), and for Ida-anti-TFR on CEM the LD$_{50}$ values were 1–2 times greater than those of free Ida (Table 1). Therefore free Ida was more cytotoxic to both E3 and CEM than Ida-anti-Ly-2.1 and Ida-anti-TFR respectively. These Ida-MoAb conjugates, however, demonstrate a 10-fold lower cytotoxicity to non-reactive cell lines (Table 1), thus indicating that their cytotoxic action was specific and resulted from their retention of antibody activity (FIG. 3).

TABLE 1

The Effect of Idarubicin-Monoclonal Antibody Conjugates on Tumor Cells.[1]

| Tumour cell line | Mean I.D.$_{50}$ values determined for | | |
|---|---|---|---|
| | Ida | Ida-anti-Ly-2.1 | Ida-anti-TFR |
| E3 | $1.2 \times 10^{-7}$ (5)[2] | $4.3 \times 10^{-7}$ (3) | $2.3 \times 10^{-6}$ (2) |
| CEM | $2.2 \times 10^{-7}$ (5) | $2.0 \times 10^{-6}$ (2) | $3.0 \times 10^{-7}$ (3) |

[1] I.D.$_{50}$ = 50% inhibition in [$^3$H]-thymidine incorporation of controls.
[2] = number of preparations tested.

The Ida-250-30.6 conjugates were slightly less active than free Ida. Free Ida had an I.D.50 of $6 \times 10^{-8}$M while the conjugate had an I.D.$_{50}$ of $3.5 \times 10^{-7}$M on the target cell line COLO 205.

Figure 5:
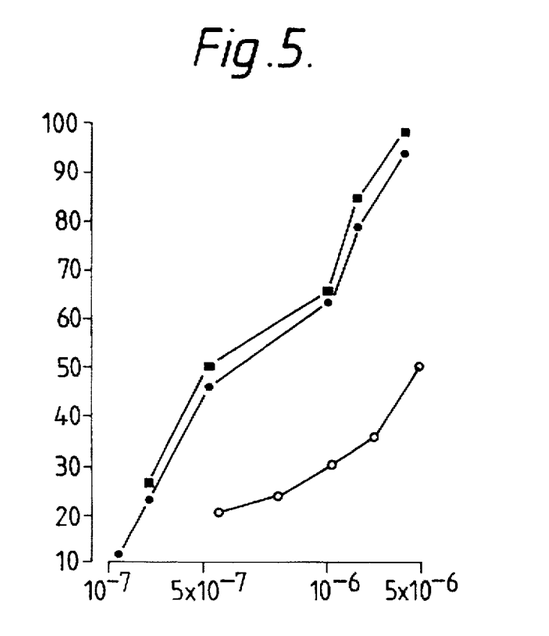
FIG. 5 represents the inhibitory effect of Ida (■), Ida-ariti-Ly-2.1, 5 mol Ida/mol antibody (●) or Ida-anti-TFR, 5 mol Ida/mol antibody (○) on (Ly-2$^+$) E3 cells in a 30 min inhibition assay where % inhibition in [$^3$H] thymidine incorporation (ordinate) is plotted against concentration of Ida(M)(abscissa)
Figure 6:
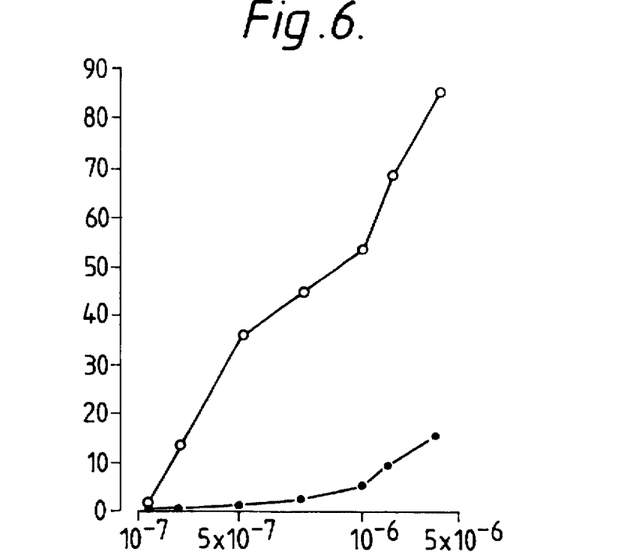
FIG. 6 represents the inhibitory effect of Ida-anti-Ly-2.1, 5 mol Ida/mol antibody (○) and conjugate plus anti-Ly-2.1 (●) on E3 target cells in a 30 min specificity assay where % inhibition in [$^3$H] thymidine incorporation (ordinate) is plotted against concentration of Ida(M) (abscissa)

To examine whether the conjugates exhibited selectively in their cytotoxic action for target cells, Ida-anti-Ly2.1 and Ida-anti-TFR were incubated for 30 minutes with E3 (Ly-2$^+$) cells, before washing away non-bound conjugate and measuring the cytotoxicity. The Ida-anti-Ly2.1 conjugate had an I.D.$_{50}$ of $6.2 \times 10^{-7}$M compared to an I.D.$_{50}$ of $5.2 \times 10^{-7}$M for free Ida (FIG. 5). By contrast, the non-reactive Ida-anti-TFR conjugate had an I.D.$_{50}$ of $5.0 \times 10^{-6}$M, i.e. 10 times greater than that for free Ida, demonstrating that the antibody-binding activity of the Ida-anti-Ly-2.1 conjugate resulted in its selective cytotoxicity. Similarly Ida-250-30.6 conjugate and free drug were incubated for 30 min with the COLO 205 (250-30.6+ve) and E3 (250-30.6–ve) cell lines before washing and subjecting it to the cytotoxicity assay. Both cell lines showed a similar dose response to free drug, i.e. $9.2 \times 10^{-7}$M for COLO 205 and $9.8 \times 10^{-7}$M for E3. However, the Ida-250-30.6 conjugate was 4 times more toxic to COLO 205 than to the antibody non-reactive E3 cell line. Similar results were obtained using the CEM cell line and Ida-anti-Ly-2.1 as a non-reactive control (data not shown). To ensure further that the cytotoxicity of Ida-MoAb conjugates for target cells was specific and occured at the antibody-binding site, we performed studies to inhibit conjugate cytotoxicity using free MoAb. At an Ida concentration of $4.0 \times 10^{-6}$M (2 ug anti-Ly-2.1), the cytotoxicity of the anti-Ly-2.1 conjugate on E3 cells was reduced by 70% upon the addition of 50 ug (250 ug/ml) of anti-Ly-2.1 (FIG. 6), indicating that the cytotoxicity of the Ida-anti-Ly-2.1 conjugate is directly related to its antibody binding ability. Similar control results were obtained with 250-30.6. It should be noted that in all assays free anti-Ly-2.1, anti-TFR and 250-30.6 were non-cytotoxic (data not shown).

In Vitro Treatment of the Murine Thymoma ITT(1)75NS E3

To assess the inhibition of growth of solid tumors, groups of CBF$_1$ mice (10 per group) inoculated s.c. with $2.0 \times 10^6$ E3 cells in the abdominal region were treated with i.v. injections of one of the following: (i) PBS; (ii) anti-Ly-2.1; (iii) Ida; (iv) Ida-anti-TFR; or (v) Ida-anti-Ly-2.1. Mice received 20 ug of Ida and/or 1200 ug of anti-Ly-2.1 respectively on days 4 and 5 (tumour size=0.1 cm$^2$) after tumour inoculation.

Figure 7:
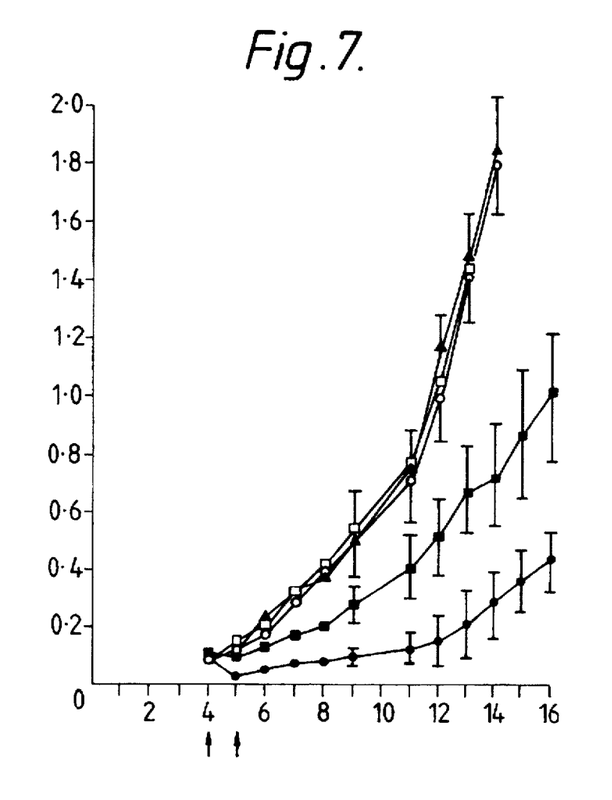
FIG. 7 represents the growth of the E3 thymoma in CBF$_1$ mice injected subcutaneously with 2×10$^6$ cells. Groups of 10 mice were given intravenous treatments denoted by an arrow; PBS (□), Ida (■), anti-Ly-2.1 (▲), Ida-anti-TFR (○) or Ida-anti-Ly-2.1 (●). Mean tumour size (cm$^2$) (ordinate) is plotted against days after tumour inoculation (abscissa). Error bars represent ± standard error of the mean.
Figure 8:
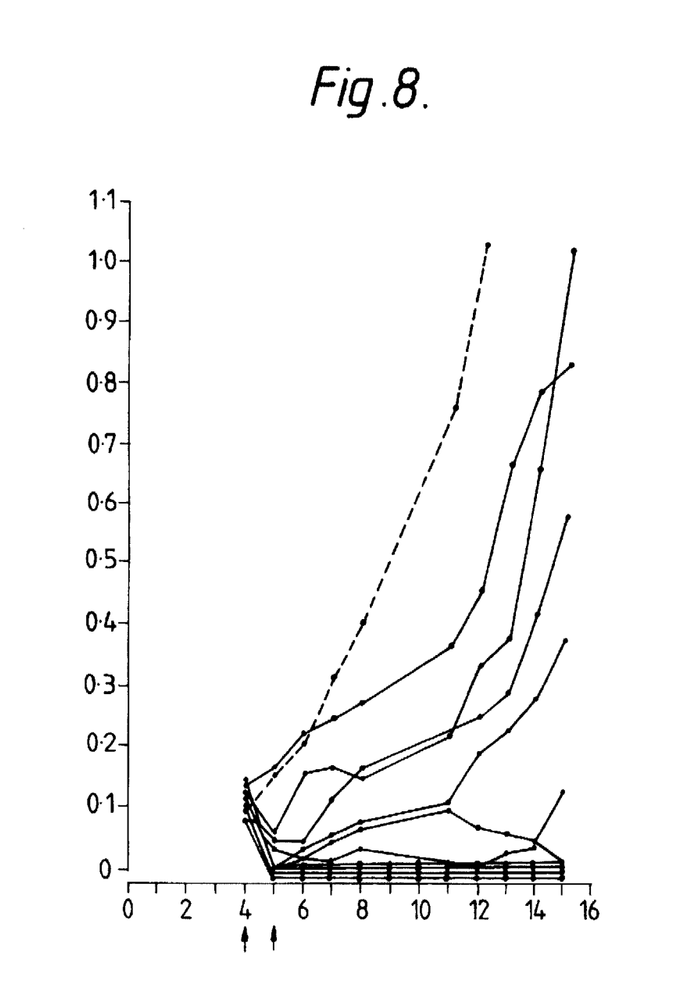
FIG. 8 represents individual tumour growth curves of CBF$_1$ mice injected subcutaneously with 2.0×10$^6$ E3 tumour cells and treated intravenously on days 4 and 5 with Ida-anti-Ly-2.1 conjugate. Tumour size (cm$^2$) (ordinate) is plotted against days after tumour inoculation (abscissa)
Figure 9:
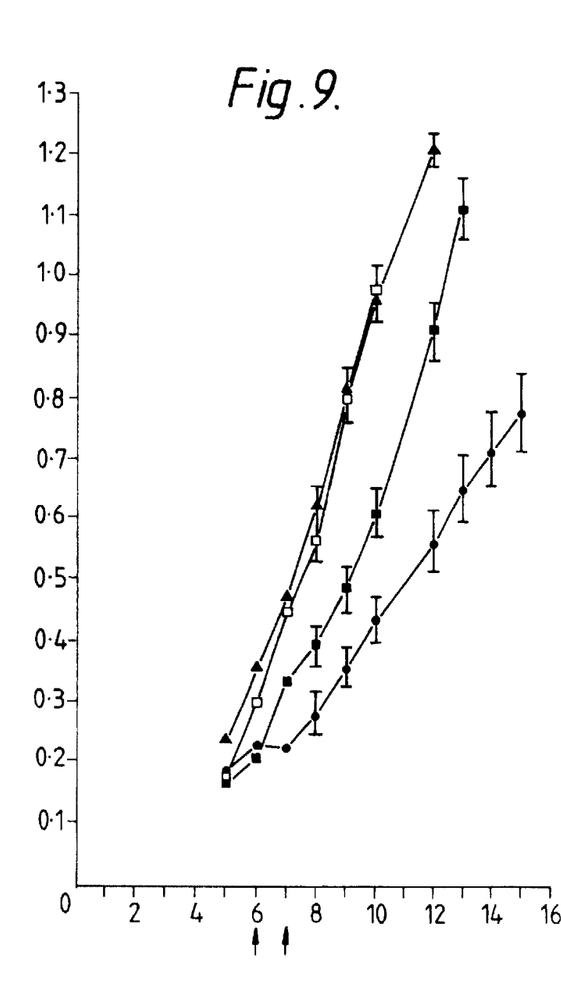
FIG. 9 represents growth of the E3 thymoma in CBF$_1$ mice injected subcutaneously with 3.0×10$^6$ cells. Groups of 10 mice were given intravenous treatments denoted by an arrow; PBS (□); anti-Ly-2.1 (▲), Ida (■) or Ida-anti-Ly-2.1 conjugate (●). Mean tumour size (cm$^2$) (ordinate) is plotted against days after tumour inoculation (abscissa). Error bars represent ± standard error of the mean.

Within 24 hours of the first treatment, the Ida-anti-Ly2.1 treated mice had a mean tumour size 20% that of PBS treated mice (i.e. an 80% decrease in tumour mass (FIG. 7)); it was evident that anti-Ly-2.1 alone and Ida covalently bound to the non-specific anti-TFR MoAb did not effect E3 tumour growth. The tumors of mice receiving Ida alone were reduced by up to 50%; however 3 of these mice died and the others had a 25% reduction in body weight. Individual tumour growth curves of mice receiving Ida-anti-Ly-2.1 demonstrated regression of 9 out of 10 tumours during the course of treatment (FIG. 8); indeed 5 out of 10 tumours completely regressed and did not reappear (>200 days), and those tumours that continued to grow at the completion of treatment (5 out of 10), grew at slower rates than the tumours of PBS and Ida-anti-TFR treated mice. A further experiment was performed to assess i.v. treatment of larger tumours using Ida-anti-Ly-2.1. Groups of CBF$_1$ mice (10 per group) were inoculated with $3.0 \times 10^6$ E3 cells, and mice then receiving 15 ug and 900 ug of Ida and anti-Ly-2.1 respectively on days 6 (tumour size=0.2 cm$^2$) and 7 after tumour inoculation (FIG. 9). The Ida-anti-Ly-2.1 treated mice had a mean tumour size 50% that of PBS treated mice, and 66% that of Ida-treated mice by day 7, this trend continuing until the termination of the study (day 18). Individual tumour growth curves of the 10 CBF$_1$ mice receiving Ida-anti-Ly-2.1 demonstrated that there were 4 regressions and 1 complete removal of tumour mass (>200 days; data not shown). Therefore Ida-anti-Ly-2.1 was effective against larger tumours and in both experiments the anti-tumour activity of Ida was considerably improved when coupled to the anti-Ly-2.1 MoAb.

In Vivo Treatment of the Human Colon Tumour COLO 205

The effect of Ida-anti-250-30.6 conjugate was assessed in nude (nu/nu) mice bearing COLO 205 xenografts.

Injection of $2 \times 10^6$ cells subcutaneously into the abdominal wall yielded a palpable lump within 4 days (approx. 0.1 cm$^2$). Groups of 10 mice were then treated with i.v. injections of one of the following: (i) PBS; (ii) 250-30.6 (iii) Ida plus 250-30.6 (non-conjugated); (iv) Ida; (v) Ida-250-30.6 conjugate. A total of 275 ug of Ida was given in a series of 5 intravenous injections on days 4, 5, 6, 10 and 12 after tumour inoculation.

Figure 11:
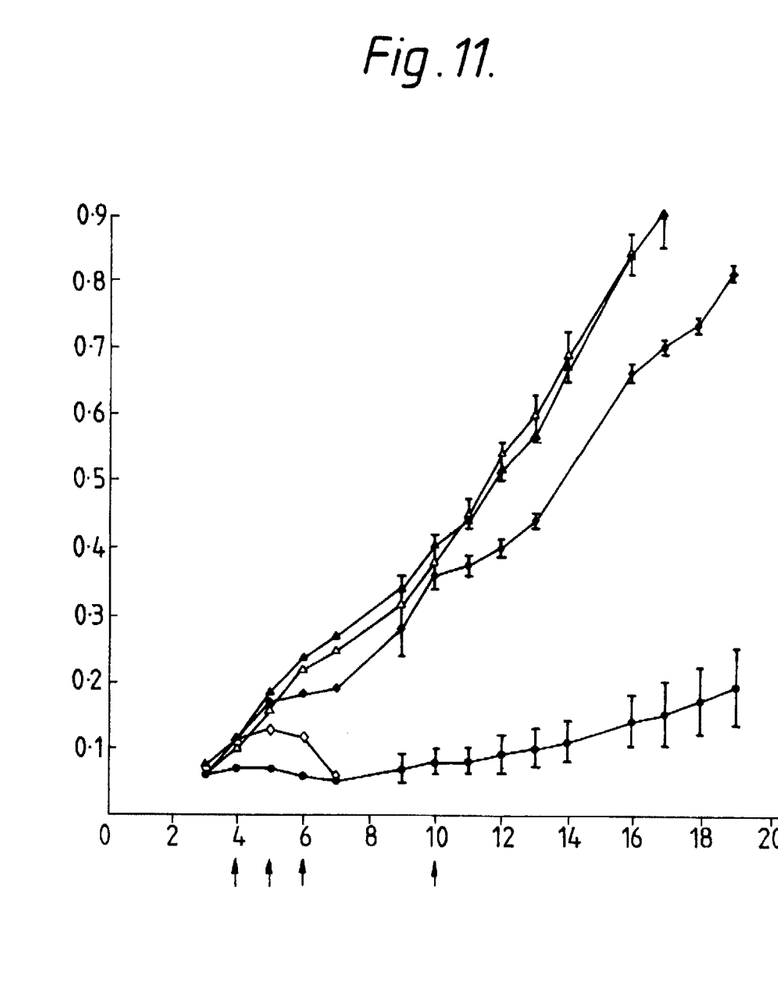
FIG. 11 represents growth of the COLO 205 human tumour xenograft in nude mice injected subcutaneously with 2×10$^6$ cells. Groups of 10 mice were given the following treatments intravenously denoted by an arrow; PBS (Δ), free Ida (♦), Ida-250-30.6 conjugate (●), mixture of Ida and 250-30.6 (◊) and 250-30.6 (▲). Mean tumour size (cm$^2$) (ordinate) is plotted against days after tumour inoculation (abscissa). Error bars represent ± standard error of the mean tumour size.
Figure 12:
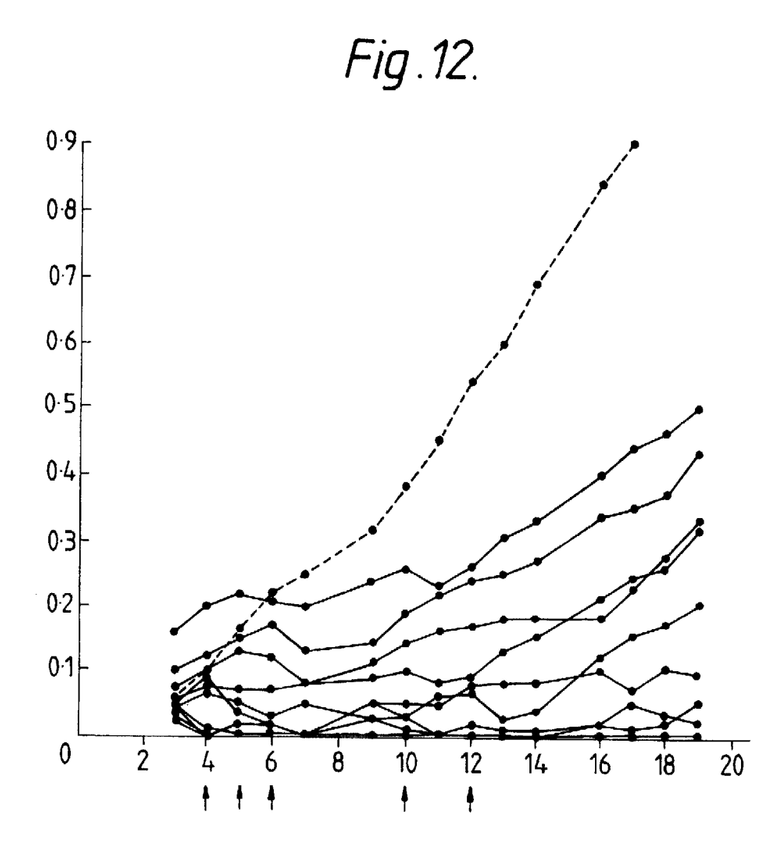
FIG. 12 represents individual tumour growth curves of xenografted nude mice which were treated i.v. (arrow) with Ida-250-30.6 conjugate. The broken line represents the mean tumour size in PBS-treated mice. Tumour size (cm$^2$) (ordinate) is plotted against days after tumour inoculation (abscissa)

No therapeutic effect was apparent in the groups of mice treated with PBS or with unconjugated 250-30.6. With Ida alone, 2 out of 10 mice survived, while all of the mice in the group receiving non-conjugated Ida plus 250-30.6 were dead by day 7, having previously shown symptoms of toxicity such as loss of weight. The mice receiving the Ida-250-30.6 conjugate showed a dramatic reduction of tumour size. These results are illustrated in FIG. 11. By contrast, tumour growth curves for individual mice (FIG. 12) showed that 5 out of the 10 mice had tumours which had regressed by day 7; these tumours then proceeded to grow, leaving 2 out of 10 mice without tumours. These mice showed no effects due to toxicity.

Intratumour Treatment

Figure 10:
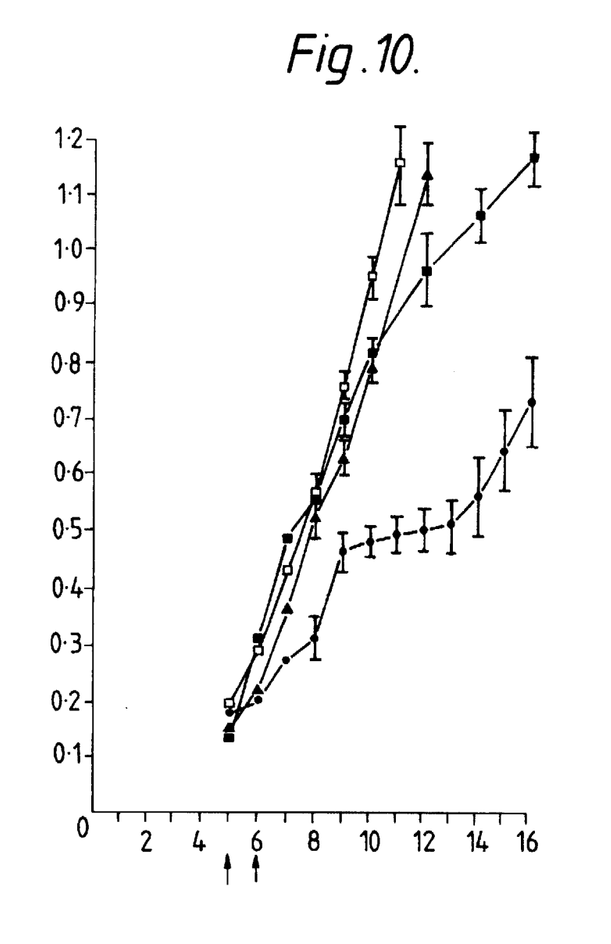
FIG. 10 represents growth of the E3 thymoma in CBF$_1$ mice injected subcutaneously with 3.0–10$^6$ cells. Groups of 10 mice were given intratumour treatments denoted by an arrow; PBS (□); anti-Ly-2.1 (▲), Ida (■) or Ida-anti-Ly-2.1 conjugate (●). Mean tumour size (cm$^2$) (ordinate) is plotted against days after tumour inoculation (abscissa). Error bars represent ± standard error of the mean.

Intratumour therapy has been shown to be a useful technique for immunotherapy of animal and human tumours. Consequently studies were performed to characterize the anti-tumour activity of Ida-anti-Ly-2.1 conjugates when administered directly into solid E3 tumour. Groups of 10 CBF$_1$ mice implanted s.c. with $3.0 \times 10^6$ E3 cells developed tumours (0.1–0.2 cm$^2$) 5 days after tumour inoculation. The treatments consisted of 2 injections on days 5 and 6 after tumour implantation, mice receiving one of the following treatments; (1) PBS; (2) Ida; (3) Anti-Ly-2.1; or (4) Ida-anti-Ly-2.1 (Total Ida=30 ug). Ida-anti-Ly-2.1 demonstrated the greatest anti-tumour activity, free Ida and anti-Ly-2.1 alone not affecting tumour growth when administered directly into the tumour. The Ida-anti-Ly-2.1 treated mice had a mean tumour size 60% that of PBS-treated mice on day 8 and 30% that of PBS-treated mice on day 13 (FIG. 10). Individual tumour growth curves (data not shown) of Ida-anti-Ly-2.1 treated mice indicated 1 complete regression whilst the remaining mice demonstrated a delayed reduction in tumour growth 3 days after the completion of treatment.

Toxicity

For acute toxicity experiments groups of 10 CBA (Ly2.1⁺) mice were given a single injection of various doses of either Ida, Ida-anti-Ly-2.1 or Ida-anti-TFR. All mice injected with Ida showed an initial weight loss of up to 25% of the original weight; however no weight loss was observed in mice treated with either Ida-MoAb conjugate. Table 2 demonstrates the toxicity of Ida and Ida-MoAb conjugates as reflected in $LD_{50}$ and $LD_{10}$ values. As shown, the $LD_{10}$ of Ida-anti-Ly-2.1 was 10.0 mg/kg of Ida as compared to only 0.75 mg/kg for free Ida. In addition the Ida-anti-TFR conjugate had an $LD_{10}$ of 8.0 mg/kg. Ida-MoAb conjugates were not tested to an $LD_{50}$ dose. These results demonstrate the greater therapeutic index of Ida-MoAb-conjugates compared with free Ida.

TABLE 2

The Effect of Idarubicin-Monoclonal Antibody Conjugates on CBA mice.

| | Ida (mg/kg) | |
|---|---|---|
| | $L.D._{10}$ | $L.D._{50}$ |
| Ida | 0.75 | 3.00 |
| Ida-anti-Ly-2.1 | 10.00 | N.T. |
| Ida-anti-TFR | 15.00 | N.T. |

N.T. = not tested

Histopathological Results

Acute effect: The intravenous administration of free Ida (1.0 mg/kg) resulted in atrophy of the white pulp in the spleen 15 days after treatment and some hypertrophy of cardiac muscle fibres (data not shown). In contrast, a single dose of Ida-anti-Ly-2.1 (2.4 mg/kg) did not cause any non-specific tissue toxicity after 15 and 30 days although some swelling of hepatocytes was observed at day 15

EXAMPLE 2

Materials and Methods

Mice (DBA/2×BALB/c)F₁ and CBA mice were produced in the Department of Pathology, University of Melbourne. Experimental groups of 10–20 mice, all of the same sex and age, were used in each experiment.

Tumour Cells

The cell lines examined in this study included the (Ly-2⁺) murine thymoma ITT(1)75NS E3 variant (E3), the (L3T4⁺) lymphoma EL4 (Horowitz et al, Science 1968 160 533–535), the human colon carcinoma Colo 205 (Semple et al, Cancer Res. 1978 38 1345–1355) and the (Ly-2⁻, L3T4⁻) human T cell leukemia CEM (Foley et al, Cancer 1965 18 522–529). Cells were maintained in vitro as described in Example 1. The P388D1 macrophage cell line was maintained in vivo by serial passage into (DBA/2×BALB/c)F₁ mice. Cells from the ascites fluid were washed and centrifuged (400 g×5 min) twice in phosphate-buffered saline (PBS, pH7.3), resuspended in PBS and injected s.c. into the abdominal-wall of mice where they developed into palpable tumour grafts. Mice were then subjected to a series of i.v. treatments and the size of the tumours was measured daily with a caliper square, measuring along the perpendicular axes of the tumours. Data was recorded as mean tumour size (product of two diameters ± standard error).

Monoclonal Antibodies

Monoclonal antibodies to the murine cell surface antigens L3T4, Ly-2 and Thy-1, which characterize distinct subpopulations of lymphocytes, were used as a model system.

MoAbs used were: (i) anti-Ly-2.1 (murine IgG2a) reactive with the murine Ly-2.1 specificity (Horgarth et al, Immunology 1982 46 135–144), (ii) H129.19 (anti-L3T4) (rat IgG2b) reactive with the murine L3T4 specificity (Pierres et al, J. Immunology 1984 132 2775–2782), and (iii) anti-Thy-1 (rat IgG2b) reactive with murine T cells (Marshak-Rothstein et al, J. Immunology 1979 122 2491–2497). The antibodies were isolated, purified and stored as described in Example 1. Antibody activity was determined by rosetting assay with sheep anti-mouse immunoglobulin (SAMG) as described in Example 1.

Preparation of Idarubicin-Monoclonal Antibody Conjugates

A MoAb (1–2 mg/ml) was mixed with a 5–20 molar excess of 14-bromo-4-demethyoxydaunorubicin (Br-Ida) dissolved in (N,N)-dimethylformamide (10 mg/ml) for 4 hours at pH8.0 (0.05M Borate buffer) and room temperature. Reaction proceeded, purification was effected and the amount of Ida incorporated in the resulting conjugate was determined as described in Example 1.

Drug Activity

Two assays (24 hours and 30 minutes) were performed to assess drug activity as described in Example 1, using cells at a concentration of from (1 to 5×10⁶/ml).

Serology

A resetting method was used throughout these experiments to determine antibody titre and numbers of L3T4⁺ and Ly-2⁺ cells. This method involved binding SAMG which also detects rat immunoglobulin (Ig) coupled to sheep red cells (SRC) to detect antibodies on the surface of lymphoid cells. Ig⁺ splenic cells had the surface Ig removed by capping with SAMG (25 ul and 2 ml cells at 10⁷/ul); cells were then kept on ice in medium containing 0.01% sodium azide to prevent resynthesis of immunoglobulin.

Results

The study was conducted in separate phases:

(a) in vitro characterization of three different Ida-MoAb conjugates, and (b) subsequent demonstration of their use in actively depleting T cell subsets before or during the rejection of a tumour cell allograft.

Preparation and Characterization of Conjugates

Figure 13:
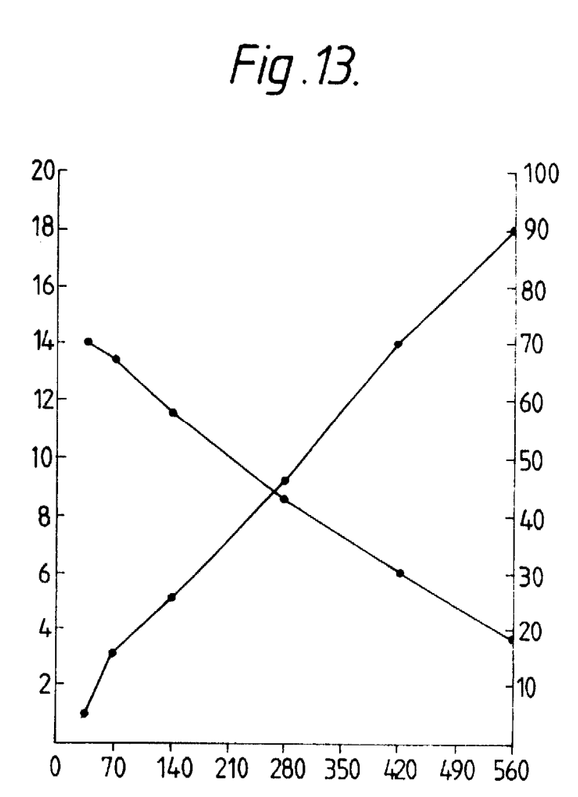
FIG. 13 shows the coupling of Idarubicin (Ida) to anti-L3T4 (0.5 mg). Moles of Ida incorporated per mole of anti-L3T4 (♦) (left hand ordinate) and protein recovery (●) (right hand ordinate) are shown as a function of the number of nmoles of Ida in the reaction mixture (abscissa)

Br-Ida was convalently coupled to MoAb against the murine L3T4, Ly-2 and Thy-1 antigens. Reaction conditions were established for the conjugation by varying the molar excess of Br-Ida added to MoAb and making a compromise between higher Ida incorporation and lower protein recoveries. Ida-anti-L3T4 (FIG. 13), Ida-anti-Ly-2.1 and Ida-anti-Thy-1 (data not shown) incorporated 3–6 molecules of Ida, with protein recoveries of greater than 50%.

Antibody Activity

Figure 14:
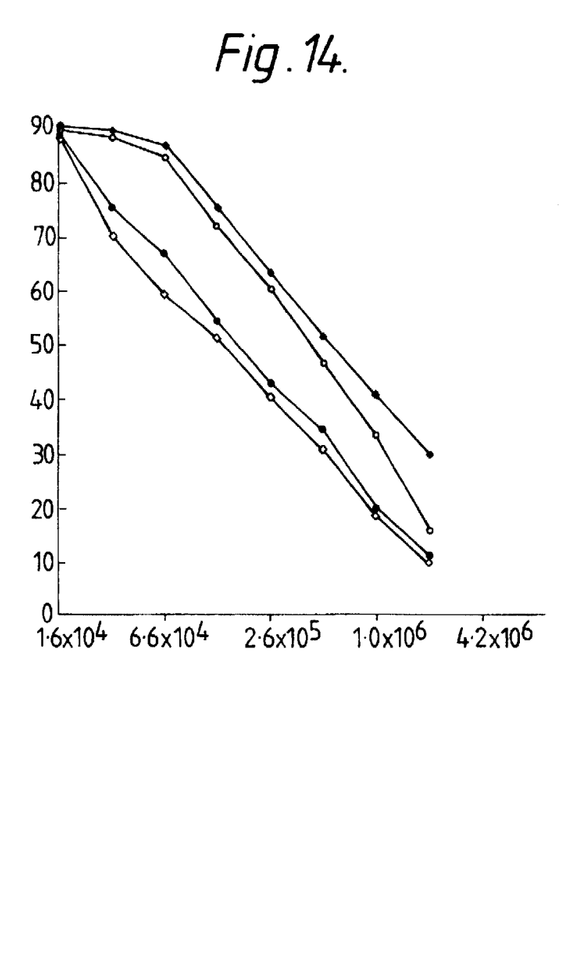
FIG. 14 shows antibody titre measured as the % rosette forming cells (ordinate) versus antibody dilution (×10$^{-1}$) (abscissa) of anti-Thy-1 conjugates on ITT(1) 75NS E3 target cells. Serial dilutions were performed upon a 1.0 mg/ml solution of either anti-Thy-1 (♦) or conjugate with 1 (○), 4 (●) or 7 (◊) mol Ida/mol anti-Thy-1.

The titres of antibody before and after conjugation were measured by the rosetting method and were determined as the dilution at which 50% of the E3 target cells demonstrated rosettes. Ida-anti-Thy-1 conjugates containing 1, 4 and 7 molecules of Ida had antibody titres of 1:425,000, 1:170,000 and 1:130,000 respectively, whilst the unmodified antibody titre was 1:550,000 (FIG. 14). Thus there is some loss of antibody activity upon conjugation to Ida; however, conjugates with less than 4 molecules of Ida-molecule to MoAb were used for in vitro and in vivo studies. Similarly, the antibody activity of both Ida-anti-Ly-2.1 and Ida-anti-L3T4 conjugates (data not shown) decreased significantly with incorporation of more than 6 molecules of Ida-molecule MoAb.

In Vitro Drug Activity

The cytotoxicity of the Ida-MoAb conjugates was tested on different reactive target cells using a 24 hour assay and compared with that free Ida. The activity of free Ida was 4–10 times greater than the Ida-MoAb conjugates, with I.D.$_{50}$ (50% inhibition in [$^3$H]-thymidine incorporation of controls) of free Ida occurring at 6.6–9.0×10$^{-8}$M against the tumour cell lines tested. It was clear that the Ida-anti-Ly-2.1 conjugate was the most cytotoxic conjugate (I.D.$_{50}$=4.3×10$^{-7}$M) when tested against the ITT(1)75NS E3 cell line, which is a variant of the native cell line enriched for the Ly-2 antigen. To examine the selectivity of conjugate action for target cells, Ida-MoAb conjugates were incubated for 3 minutes with target cells, before washing away unbound conjugate and measuring the cytotoxicity. Using this 30 min assay, the non-reactive Ida-MoAb conjugates had an I.D.$_{50}$ 10–50 times greater than that of free Ida, demonstrating that antibody binding was essential for Ida-MoAb conjugate cytotoxicity. It should be noted that none of the MoAb used in the study had a cytotoxic action on target cells in vitro in the absence of complement. Results are summarized in Table 3.

TABLE 3

The effect of Idarubicin-monoclonal anitbody conjugates
Mean ID$_{50}$ on tumour cells.[1]

| Tumour cell line | Assay | Mean I.D.$_{50}$ values (Ida (M)) determined for | | |
|---|---|---|---|---|
| | | Ida | Ida-anti-Ly-2.1 | Ida-anti-L3T4 | Ida-anti-Thy-1 |
| E3 | 24 hr[2] | 7.8 × 10$^{-8}$ | 4.3 × 10$^{-7}$ | N.T. | 9.0 × 10$^{-7}$ |
|  | 30 min[3] | 1.8 × 10$^{-7}$ | 4.3 × 10$^{-7}$ | N.T. | 1.2 × 10$^{-6}$ |
| EL4 | 24 hr | 6.6 × 10$^{-8}$ | N.T. | 6.0 × 10$^{-7}$ | N.T. |
|  | 30 min | 1.6 × 10$^{-7}$ | N.T. | 6.2 × 10$^{-7}$ | N.T. |
| CEM | 24 hr | 9.0 × 10$^{-8}$ | N.T. | N.T. | N.T. |
|  | 30 min | 2.2 × 10$^{-7}$ | 6.0 × 10$^{-6}$ | N.T. | N.T. |
| Colo 205 | 24 hr | 8.0 × 10$^{-8}$ | N.T. | N.T. | N.T. |
|  | 30 min | 1.2 × 10$^{-7}$ | N.T. | 4.0 × 10$^{-6}$ | 5.8 × 10$^{-6}$ |

[1] I.D.$_{50}$ = 50% inhibition in [$^3$H]-thymidine incorporation of controls
[2] using a 24 hour cytotoxicity assay
[3] using a 30 minute assay
N.T. = not tested.

In Vivo Potency of Idarubicin-Monoclonal Antibody Conjugates

Figure 15:
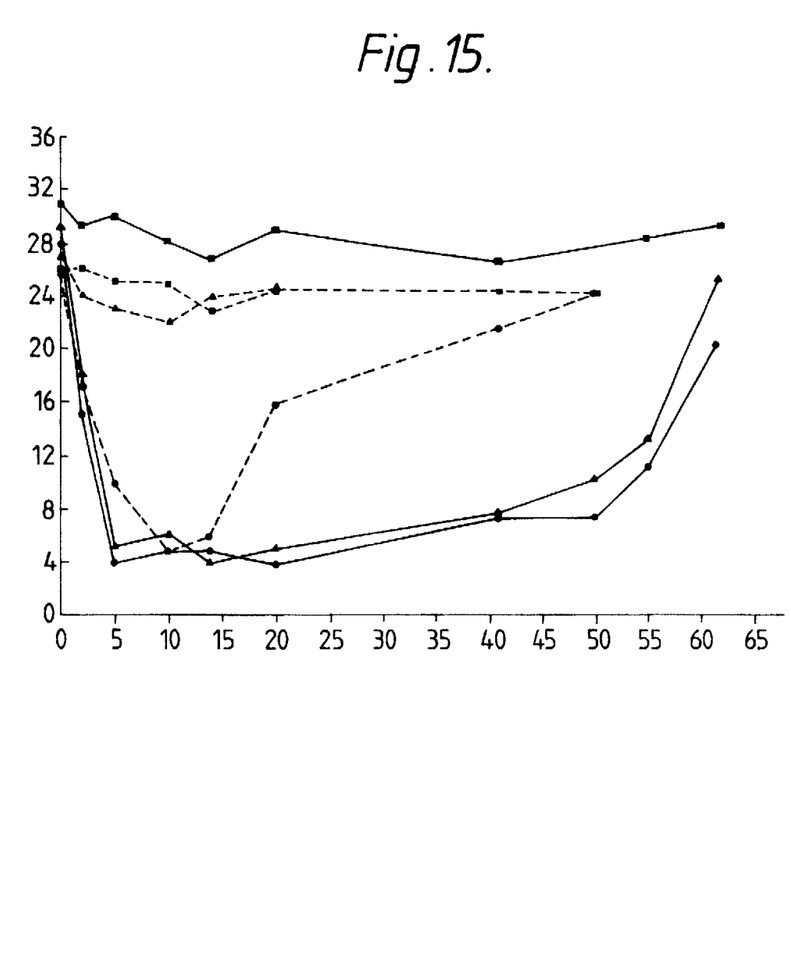
FIG. 15 shows the effect of Ida-MoAb and MoAb treatment on the number of L3T4$^+$ and Ly-2$^+$ cells in the spleen in Ida-anti-L3T4 treated (●—●), anti-L3T4 treated (▲—▲), Ida-anti-Ly-2.1 treated (●—●), anti-Ly-2.1 treated (▲—▲) or untreated (□—□) mice in which % rosette forming cells (ordinate) is plotted against time in days (abscissa)

The in vivo immunosuppressive potency of the Ida-MoAb conjugates was compared to that of MoAb alone by testing the ability of the conjugates to selectively deplete L3T4$^+$ or Ly-2$^+$ cells from the spleen. CBA mice received 4 i.v. injections of anti-Ly-2.1 or anti-L3T4 conjugate (30 ug Ida/1.5 mg MoAb) on days 0, 2, 5 and 10, and the number of Ly-2$^+$ or L3T4$^+$ cells in the spleen was monitored by the rosetting assay. For each treatment the spleen cells of two treated mice were examined on each day, and the results averaged (FIG. 15). There was a rapid fall in the number of L3T4$^+$ cells from approximately 30% of total spleen cells in normal mice on day 0 to approximately 4% in Ida-anti-L3T4 treated mice by day 20. These L3T4$^+$ cells remained depleted for more than 60 days before a gradual increase was seen. The depletion after in vivo treatment with anti-L3T4 alone also led to a sharp decrease in L3T4$^+$ cell numbers (30% to 5%).

The Ida-anti-Ly-2.1 conjugate decreased spleen Ly-2$^+$ cell numbers from 25% to 5% by day 10; however, the number of Ly-2$^+$ cells began to increase by day 15, and returned to normal by day 40–50. It was of interest that the anti-Ly-2.1 MoAb alone was unable to deplete Ly-2$^+$ cells significantly; variation in the numbers of Ly-2$^+$ and L3T4$^+$ cells in untreated control mice was assumed to be due to natural variation between mice. Thus it was clear that both Ida-anti-L3T4 and Ida-anti-Ly-2.1 could deplete L3T4$^+$ or Ly-2$^+$ cells respectively from the spleens of treated mice for more effectively than the MoAb alone. The effect of the Ida-anti-Ly-2.1 conjugate is important, as the anti-Ly-2.1 MoAb is completely without effect when used alone, but can be coverted to a potent immunosuppressive agent when coupled to Ida. Depletion sustained by the drug-MoAb conjugates was therefore suitable for the examination of the role of Ly-2$^+$ and L3T4$^+$ cells in vivo in the graft rejection response.

Effect of Ida-anti-L3T4, Ida-anti-Ly-2.1 and Ida-anti-Thy-1 on Tumour Graft Survival In these experiments, Ida-anti-L3T4, Ida-anti-Ly-2.1 and Ida-anti-Thy-1 conjugates were used to increase the survival time of P388D1 tumour grafts in CBA mice, the allografts being across H-2 (Class I and II) and non-H-2 barriers.

(a) Combined Conjugate Treatment

Figure 16:
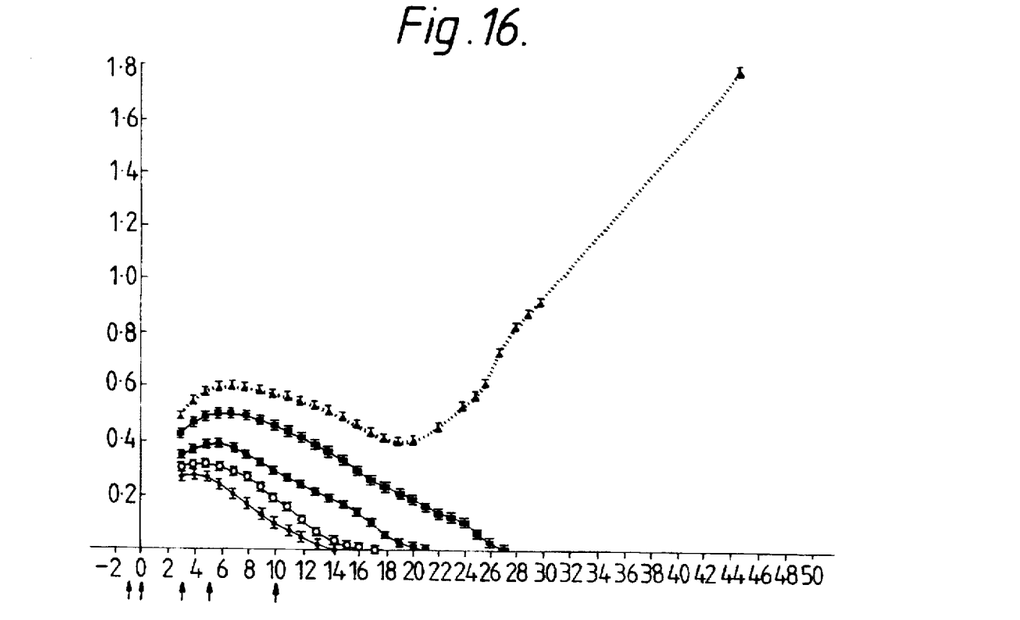
FIG. 16 shows the effect of combined Ida-MoAb conjugate treatment on the survival of a P388D1 tumour graft (across H-2 and non H-2 differences) in CBA mice. Groups of 10–15 mice were injected subcutaneously with 8.0×10$^6$ P388D1 tumour cells and received one of the following intravenously (arrow): (i) PBS (♦), (ii) anti-L3T4 and anti-Ly-2.1 (○), (iii) Ida-anti-L3T4 (■), (iv) Ida-anti-Ly-2.1 (●) and (v) Ida-anti-L3T4 and Ida-anti-Ly-2.1 (▲). Mean tumour size (cm$^2$) (ordinate) is plotted against days after tumour inoculation (abscissa). Error bars represent ± standard error of the mean.

Groups of 10–15 CBA mice were injected s.c. with 8.0×10$^6$ P388D1 tumour cells and received i.v., on days −1, 0 (=day of tumour inoculation), 3, 5 and 10, one of the following: (i) PBS, (ii) anti-L3T4 and anti-Ly-2.1, (iii) Ida-anti-L3T4, (iv) Ida-anti-Ly-2.1 and (v) Ida-anti-L3T4 and Ida-anti-Ly-2.1. The total amount of Ida and MoAb received was 125 ug and 5.75 mg respectively. The tumour grafts of both PBS and MoAb treated mice survived for 14–17 days with a maximum mean tumour size of 0.31 cm$^2$, demonstrating that both unconjugated MoAb together were unable to effectively deplete L3T4$^+$ and Ly-2$^+$ cells such that the tumour graft could survive (FIG. 16). In addition, Ida-anti-Ly-2.1 or Ida-anti-L3T4 alone were only able to prolong graft survival (day 20–28) with maximum mean tumour sizes of 0.40 cm$^2$ to 0.50 cm$^2$. It is likely that Ida-anti-Ly-2.1 or Ida-anti-L3T4 alone did not remove all T cells, and a strong antigenic challenge (as seen with whole MHC differences) was able to stimulate the remaining Ly-2$^+$ and L3T4$^+$ cells to proliferate and evoke a rejection response. By contrast, a combination of both Ida-anti-Ly-2.1 and Ida-anti-L3T4 conjugates enabled 14/15 P388D1 tumour grafts to evade rejection,and increase in size until mice were sacrificed (day 50-2.00 cm$^2$). It was noted that a few of these conjugate-treated P388D1 tumours demonstrated some regression in size from days 8 to 16; however, continual depletion of L3T4$^+$ and Ly-2$^+$ cells (day 10) enabled the P388D1 tumour grafts to establish consistent tumour growth.

(b) Ida-anti-Thy-1 Conjugate

Figure 17:
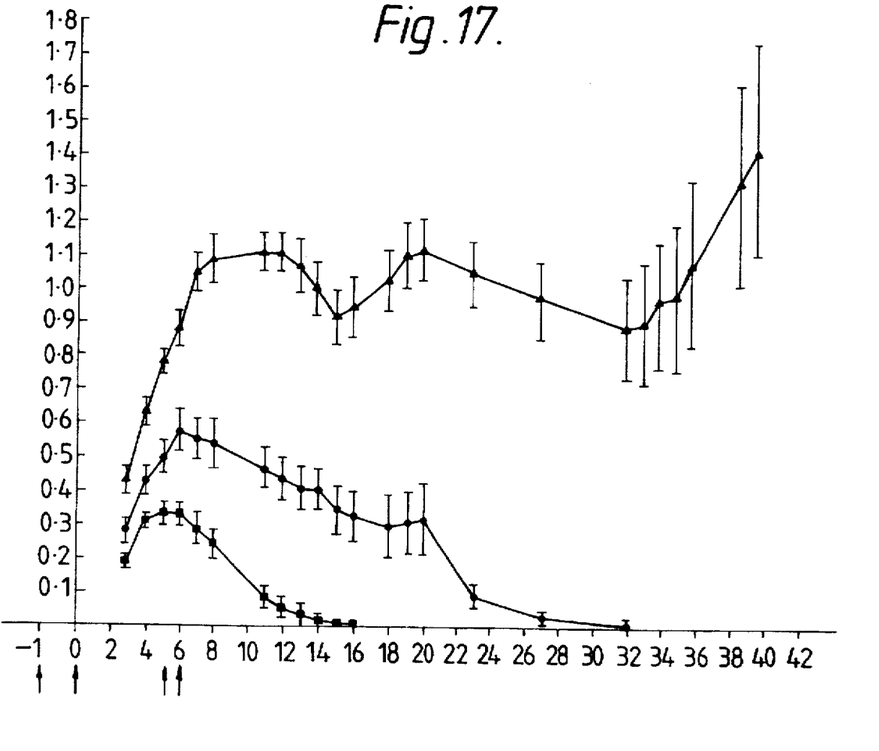
FIG. 17 shows the effect of Ida-anti-Thy-1 conjugate on the survival of a P388D1 tumour graft in CBA mice. Groups of 10 mice were injected subcutaneously with 1.0×10$^7$ P388D1 tumour cells and received intraveneously (arrow) one of the following: (i) PBS (□), (ii) anti-Thy-1 (●) and (iii) Ida-anti-Thy-1 (▲). Mean tumour size (cm$^2$) (ordinate) is plotted against days after tumour inoculation (abscissa). Error bars represent ± standard error of the mean.

Groups of 10 CBA mice were injected s.c. with 10$^7$ P388D1 tumour cells and received one of the following i.v. on days −1, 0, 5 and 6: (i) PBS, (ii) anti-Thy-1 and (iii) Ida-anti-Thy-1. The total amount of Ida and anti-Thy-1 received was 130 ug and 5.4 mg respectively, and the tumour grafts of PBS-treated mice survived for 15 days. The anti-Thy-1 MoAb alone maintained tumour graft survival for 28–32 days, with a maximum mean tumour size of 0.58 cm$^2$ (day 6) (FIG. 17). Of the Ida-anti-Thy-1 treated mice, 30% of the tumour grafts were rejected completely by day 40, while the remaining 70% continued to grow, eventually (day 32) enabling the mean tumour size of the group to increase. Therefore Ida-anti-Thy-1, like the combination of Ida-anti-Ly-2.1 and Ida-anti-L3T4, was capable of depleting Ly-2$^+$ and L3T4$^+$ cells such that a majority of P388D1 tumour grafts survived in CBA mice in the absence of a normally rapid rejection response.

EXAMPLE 3

Figure 18:
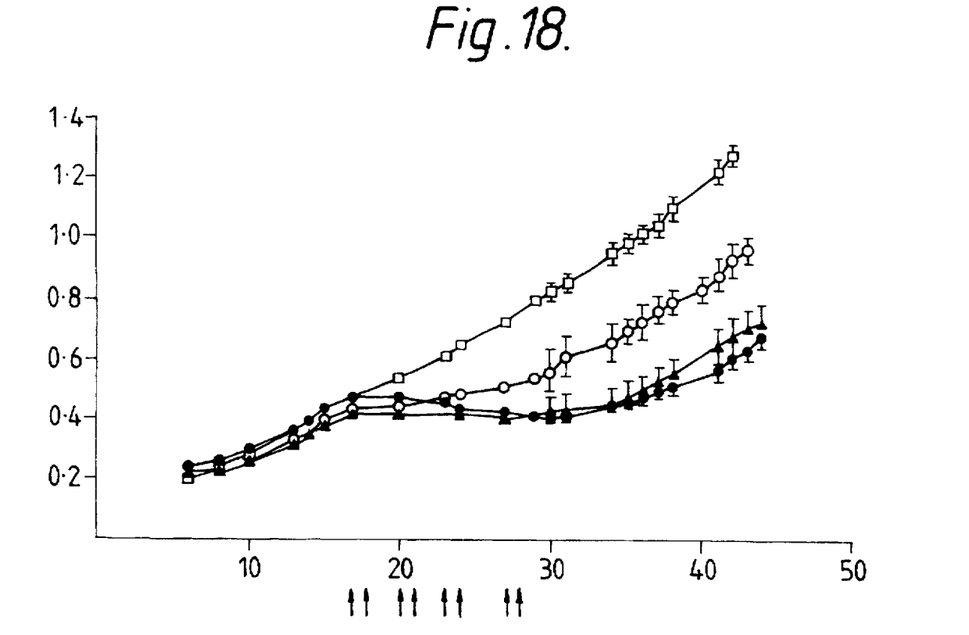
FIG. 18 shows growth of COLO 205 (30.6$^+$, 17.1$^+$) xenograft in nude mice injected with 8×10 cells/mouse. Groups of 10 mice were treated intraperitoneally, denoted by an arrow, with PBS (□); 17.1-Ida (○); 30.6-Ida (Δ) or a mixture of 30.6-Ida and 17.1-Ida (●). Mean tumour size (cm$^2$)(ordinate) is plotted against days after tumour inoculation (abscissa). Error bars represent ± standard error of the mean. The total dose of Ida was 200 μg.

Conjugates were prepared according to the procedure described in Example 1 between Ida and the monoclonal antibody 17.1 (Thompson et al, Proc. Natl. Cancer Inst. 70, 409–419, 1983. Murine IGG2A) and between Ida and the monoclonal antibody 30.6 (Thompson et al, Br. J. Cancer 47, 595–605, 1983. Murine IGG2A). Human colon carcinoma Colo 205 cells (30.6$^+$, 17.1$^+$) were inoculuated s.c. into nude mice at 8×10$^6$ cells/mice as described in Example 2. The inoculated mice were then subjected to a series of i.p. treatments. The size of the tumours was measured with a caliper square, measuring along the perpendicular axes of the tumours. Data was recorded as mean tumour size (product of two diameters ± standard error). The results are shown in FIG. 18.

EXAMPLE 4

Figure 19:
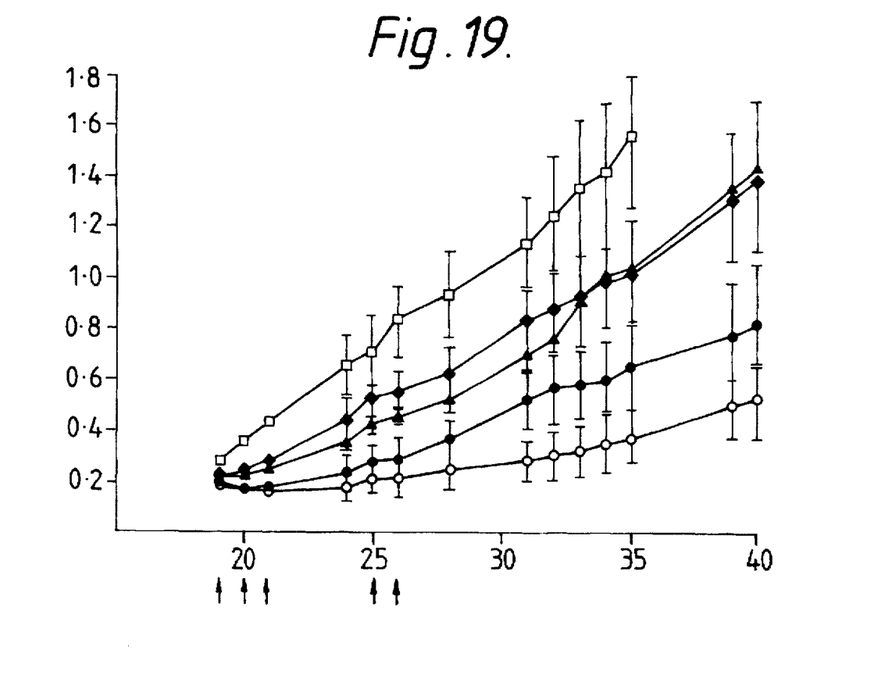
FIG. 19 hows growth of LIM2210 human colon tumour xenograft in nude mice implanted with tumour fragment (1–5 mg). Groups of 10 mice were treated intravenously, denoted by an arrow, with PBS (□); 17.1-Ida (♦); JGT-13-Ida (▲); 27.1-Ida (●), 30.6-Ida (○). Mean tumour size (cm$^2$)(ordinate) is plotted against days after tumour inoculation (abscissa). Error bars represent ± standard error of the mean. The total dose of Ida was 80 μg.

Conjugates were prepared according to the procedure described in Example 1 between Ida and the monoclonal antibody 17.1, between Ida and the monoclonal antibody JGT-13 (mouse IGG1, reactive with Carcenoembryomic antigen on colon carcinoma but not with normal tissues), between Ida and the monoclonal antibody 27.1 (mouse IGG1, reactive with human milk fat globule antigen on a number of colon tumors) and between Ida and the monoclonal antibody 30.6. A LIM2210 human colon tumor xenograft (1–5 mg) was implanted sc in nude mice. The implanted mice were then subjected to a series of i.v. treatments. The size of the tumours was measured with a caliper square, measuring along the perpendicular axes of the tumours. Data was recorded as mean tumour size (product of two diameters± standard error). The results are shown in FIG. 19.

We claim:

1. An immunoglobulin conjugate comprising idarubicin conjugated at the C-14 position to (a) a monoclonal antibody specific for an antigen selected from the group consisting of a human neoplasm and a T lymphocyte cell surface antigen, or (b) a fragment of said monoclonal antibody comprising at least one site which specifically binds said antigen, wherein at least 50% of said idarubicin is conjugated to said monoclonal antibody or fragment thereof at the C-14 position through an ester linkage.

2. The immunoglobulin conjugate of claim 1, wherein said monoclonal antibody or fragment thereof is specific for a suppressor T lymphocyte cell surface antigen.

3. The immunoglobulin conjugate of claim 1, wherein from two or eight idarubicin molecules are covalently linked to said antibody molecule.

4. The immunoglobulin conjugate of claim 1, wherein said monoclonal antibody or fragment thereof is specific for human transferrin receptor.

5. The immunoglobulin conjugate of claim 1, wherein said monoclonal antibody or fragment thereof is specific for a neoplasm selected from the group consisting of a breast neoplasm, colon neoplasm, lung neoplasm, prostate neoplasm, and ovary neoplasm.

6. The immunoglobulin conjugate of claim 1, wherein said idarubicin is conjugated to said monoclonal antibody or fragment thereof by reacting 14-haloidarubicin with said monoclonal antibody or fragment thereof in dimethylformamide in a borate buffer.

7. The immunoglobulin conjugate of claim 6, wherein said reacting is conducted at a pH of 8.0.

8. A pharmaceutical composition comprising a pharmaceutically acceptable carrier or diluent, and as an active ingredient, an immunoglobulin conjugate comprising idarubicin conjugated at the C-14 position to (a) a monoclonal antibody specific for an antigen selected from the group consisting of a human neoplasm and a T lymphocyte cell surface antigen, or (b) a fragment of said monoclonal antibody comprising at least one site which specifically binds said antigen, wherein at least 50% of said idarubicin is conjugated to said monoclonal antibody or fragment thereof at the C-14 position through an ester linkage.

9. The composition of claim 8, wherein said monoclonal antibody or fragment thereof is specific for a suppressor T lymphocyte cell surface antigen.

10. The composition of claim 8, wherein from two to eight idarubicin molecules are covalently linked to said antibody molecule.

11. The composition of claim 8, wherein said monoclonal antibody or fragment thereof is specific for human transferrin receptor.

12. The composition of claim 8, wherein said monoclonal antibody or fragment thereof is specific for a neoplasm selected from the group consisting of a breast neoplasm, colon neoplasm, lung neoplasm, prostate neoplasm, and ovary neoplasm.

* * * * *

UNITED STATES PATENT AND TRADEMARK OFFICE
CERTIFICATE OF CORRECTION

PATENT NO. : 5,798,097
DATED      : August 25, 1998
INVENTOR(S): Ian F.C. MCKENZIE, et al.

It is certified that error appears in the above-identified patent and that said Letters Patent is hereby corrected as shown below:

On the title page, Item [54], the title, is incorrect.
It should read:

--IDARUBICIN IMMUNOGLOBULIN CONJUGATES--

Signed and Sealed this

Thirtieth Day of March, 1999

Attest:

Q. TODD DICKINSON

Attesting Officer

Acting Commissioner of Patents and Trademarks